(12) United States Patent
Modi

(10) Patent No.: US 6,620,519 B2
(45) Date of Patent: Sep. 16, 2003

(54) SYSTEM AND METHOD FOR INHIBITING CORROSION OF METAL CONTAINERS AND COMPONENTS

(75) Inventor: Paresh R. Modi, Highlands Ranch, CO (US)

(73) Assignee: Lockheed Martin Corporation, Bethesda, MD (US)

(*) Notice: Subject to any disclaimer, the term of this patent is extended or adjusted under 35 U.S.C. 154(b) by 0 days.

(21) Appl. No.: 09/839,606

(22) Filed: Apr. 20, 2001

(65) Prior Publication Data

US 2001/0054454 A1 Dec. 27, 2001

Related U.S. Application Data (63) Continuation-in-part of application No. 09/757,387, filed on Jan. 8, 2001, now abandoned, which is a continuation-in-part of application No. 09/289,373, filed on Apr. 8, 1999, now abandoned.
(60) Provisional application No. 60/081,094, filed on Apr. 8, 1998.

(51) Int. Cl.[7] .............................................. B32B 15/04
(52) U.S. Cl. ..................... 428/450; 428/686; 428/34.1; 428/457; 428/469; 244/158 R; 244/172; 60/200.1; 60/257
(58) Field of Search ................................. 428/450, 686, 428/34.1, 35.8, 457, 469; 198/241; 137/899.2, 899.4; 244/158 R, 172; 60/200.1, 257

(56) References Cited

U.S. PATENT DOCUMENTS

| | | | |
|---|---|---|---|
| 2,023,496 A | 12/1935 | Todd | 87/5 |
| 2,348,678 A | 5/1944 | George | 44/56 |
| 2,714,963 A * | 8/1955 | Lester et al. | 137/101.11 |
| 3,615,895 A | 10/1971 | Von Freyhold et al. | 148/6.15 R |
| 3,787,226 A | 1/1974 | Iglehart et al. | 117/66 |

(List continued on next page.)

FOREIGN PATENT DOCUMENTS

| | | |
|---|---|---|
| GB | 127772 | 6/1919 |
| GB | 847 981 | 9/1960 |
| JP | 51-136539 | 11/1976 |
| JP | 56-27894 | 3/1981 |
| JP | 58-126989 | 7/1983 |
| JP | 59-20476 | 2/1984 |
| JP | 61-295379 | 12/1986 |
| JP | 63-159477 | 7/1988 |
| JP | 1-289873 | 11/1989 |
| JP | 2-125884 | 5/1990 |
| WO | WO 99/51362 | 10/1999 |

OTHER PUBLICATIONS

Japanese Patent JP 5281615A (1977), English Abstract.

*Primary Examiner*—John Sheehan
*Assistant Examiner*—Andrew L. Oltmans
(74) *Attorney, Agent, or Firm*—Marsh Fischmann & Breyfogle LLP (57) ABSTRACT

A method and system for inhibiting corrosion of aluminum and other metal-containing components and structures exposed to water is disclosed. In one embodiment, the silicate solution is used as a test fluid medium for structural testing of aluminum-alloy or other metal container structures including propellant tanks, in which a structure filled with the medium is then subjected to various structural load testing. In another embodiment, the silicate solution is used as a test medium for proof pressure hydrostatic or load testing of launch vehicle booster tanks. The silicate film protects the underlying base metal surface against corrosion during these tests. The film also protects the base metal surface in normal atmospheric conditions from exposure to humidity and other atmospheric moisture after removal of the test medium from the propellant tank following completion of testing.

11 Claims, 7 Drawing Sheets

U.S. PATENT DOCUMENTS

| | | | |
|---|---|---|---|
| 4,146,410 A | 3/1979 | Reinhold | 148/6.2 |
| 4,238,350 A | 12/1980 | Larsen et al. | 252/392 |
| 4,380,268 A | 4/1983 | Martin | 166/304 |
| 4,426,309 A | 1/1984 | Abel et al. | 252/75 |
| 4,439,416 A | 3/1984 | Cordon et al. | 424/47 |
| 4,780,347 A * | 10/1988 | Cohen | 428/34.2 |
| 4,846,989 A | 7/1989 | Killa | 252/99 |
| 5,232,514 A | 8/1993 | Van Sciver et al. | 134/26 |
| 5,342,578 A | 8/1994 | Agrawal et al. | 422/13 |
| 5,375,378 A | 12/1994 | Rooney | 451/38 |
| 5,389,405 A | 2/1995 | Purnell et al. | 427/387 |
| 5,399,210 A | 3/1995 | Miller | 148/273 |
| 5,427,709 A | 6/1995 | Antin et al. | 352/135 |
| 5,451,431 A | 9/1995 | Purnell et al. | 427/387 |
| 5,700,523 A | 12/1997 | Petrole et al. | 422/397.8 |
| 5,702,768 A | 12/1997 | Orr | 427/421 |
| 5,901,071 A | 5/1999 | Sakai et al. | 364/578 |
| 5,938,861 A | 8/1999 | Inoue et al. | 148/247 |
| 5,964,928 A | 10/1999 | Tomlinson | 106/14.21 |
| 6,022,425 A | 2/2000 | Nelson et al. | 148/272 |
| 6,027,580 A | 2/2000 | McCormick | 148/265 |

* cited by examiner

SYSTEM AND METHOD FOR INHIBITING CORROSION OF METAL CONTAINERS AND COMPONENTS

CROSS-REFERENCE TO RELATED APPLICATION

This application is a continuation-in-part of U.S. patent application Ser. No. 09/757,387, entitled "SYSTEM AND METHOD FOR INHIBITING CORROSION OF METAL CONTAINERS AND COMPONENTS", filed Jan. 8, 2001 now abandoned, which is a continuation-in-part of U.S. patent application Ser. No. 09/289,373, filed Apr. 8, 1999 now abandoned, which is a continuation-in-part of U.S. Provisional application Ser. No. 60/081,094 filed Apr. 8, 1998, the contents of all of which are incorporated by reference herein as if each were set forth herein in full.

FIELD OF THE INVENTION

The present invention relates generally to methods for inhibiting corrosion of metal-containing surfaces that are exposed to aqueous solutions for short or prolonged periods and, in particular, relates to processes for testing tanks, containers, and other structures in which water is used as a test medium that is brought into contact with one or more surfaces of such structures. The present invention relates also to methods for inhibiting corrosion of metal surfaces exposed to normal atmospheric conditions, including environments in which humidity may not be controlled.

BACKGROUND OF THE INVENTION

Various structures having aluminum or other metallic surfaces may be subject to testing using water or water-containing solutions or materials. Such testing generally involves filling a structure to be tested with water or an aqueous solution, subjecting the structure to various stresses, and then examining the walls of the structure, and in particular, any seals or joints in the walls, for deformation, leakage of water, or other irregularities. When such testing is conducted using source water or a similar water-containing solution over short periods (e.g., of less than four hours), minor discoloring corrosion of aluminum-containing surfaces and components of the structure may occur. When testing is conducted using source water or a similar water-containing solution over extended periods (e.g., of more than four hours), pitting corrosion and other substantial degradation of metal-containing surfaces and components may occur. This, in turn, can diminish the integrity of the structure being tested.

Space launch vehicles are generally constructed of components comprised of lightweight aluminum alloys. For example, the interior walls of booster tanks used in propulsion, and components within the booster tanks, are often fabricated from aluminum alloy materials. To evaluate the strength and integrity of such booster tanks, it is desirable to conduct structural testing, such as static load or proof pressure hydrostatic testing. This testing generally involves filling the booster tanks with a test medium, such as water, for periods varying from one to seven weeks, or more. However, the use of source water or a similar aqueous solution as a test medium, typically results in substantial corrosion and degradation of the interior aluminum alloy walls and components of the booster tank. Such corrosion may lead to undesirable deposits of materials on the walls and components of the booster tank. Such deposits are incompatible with liquid oxygen and rocket propellant fuels that may fill the booster tank, can be a fire hazard, and may impair the performance of working parts exposed to these propellants such as the rocket propellant engine. The interior walls of such booster tanks may be complex structures, having ridges, such as may be found in isogrid structures, and other test components that extend radially inwardly from the wall, into the interior cavity of the booster tank, making difficult the application of paint or other conversion coatings on such walls to protect them from corrosion.

A further concern for space launch vehicles is that such structures may be produced many months before projected use. Such vehicles may have to be transported over long distances from the point of production to the point of use. During transportation and storage, it may not always be possible to maintain such vehicles in a controlled environment, and they may be exposed to atmospheric moisture than can cause corrosion of aluminum-containing surfaces. It is therefore desirable to protect such aluminum-containing surfaces from corrosion during fluid testing and also later during transportation and storage, prior to use.

SUMMARY OF THE INVENTION

An object of the present invention is to provide a method for protecting the aluminum alloy and other metal surfaces of tanks, containers, and other structures from corrosion that may occur when such surfaces are exposed to an aqueous media (e.g., during testing, such as performance or validation testing).

A further object of the present invention is to provide a method for inhibiting corrosion of metal-containing surfaces that may be exposed to an aqueous medium or normal atmospheric conditions such as a humid environment.

The present invention relates to a system and method for inhibiting corrosion of metal-containing surfaces that may occur when such surfaces are exposed to water or an aqueous solution, such as during testing processes. More specifically, the invention is directed to a method for inhibiting corrosion through the use of an alkali metal silicate as an additive to the water or aqueous solution that will be brought into fluid contact with a metal-containing surface.

In one aspect of the invention, the method may include the steps of bringing water combined with an alkali metal silicate into contact with an aluminum-containing surface and maintaining such contact between the mixture of water and silicate and the aluminum-containing surface for at least a first period of time. Contacting the mixture of water and silicate with such a surface results in the formation of a thin silicate film on the surface that protects the aluminum-containing surface from corrosion. The addition of this mixture of silicate and water, in appropriate concentrations, thus functions to inhibit the corrosion that ordinarily results from exposure of such a surface to source water or a solution containing source water. In one embodiment, the alkali metal silicate comprises sodium silicate. The same effect may be achieved where the surface comprises stainless steel, alloy/carbon steel, and other metallic materials having low resistance to corrosion.

In another aspect of the present invention, the method includes the steps of forming a test medium comprised of an alkali metal silicate and water, and contacting the silicate and water test medium with an aluminum-containing surface to form a protective film on the surface during the testing process. The step of forming the combination of alkali metal silicate and water may comprise the step of mixing the silicate with water, in appropriate concentrations, to form a silicate solution, preliminary to the step of contacting the solution with the aluminum-containing surface. The step of forming the combination of alkali metal silicate and water may alternatively include the step of contacting the aluminum-containing surface of a structure to be tested with water and then mixing silicate with the water to form a silicate solution test medium that in turn forms a protective film on the aluminum surface. In one embodiment of the invention, the silicate comprises sodium silicate.

For purposes of enhancing the anti-corrosive effect of the invention, the water to be combined with the silicate may comprise deionized water. Deionized water substantially lacks the ionic impurities that can contribute to corrosion of aluminum and other metal surfaces in contact with this water. In one embodiment, the invention includes a preliminary step of deionizing water to be used in the test medium, before the step of forming the test medium.

A further aspect of the method of the present invention is directed to protecting the aluminum-containing inner wall surface of a launch vehicle propellant tank during testing of such tank, where the test medium is comprised of deionized water. In this aspect of the invention the method generally includes the steps of contacting an aqueous test medium comprising a sodium silicate solution with at least a first section of the inner wall surface of the tank, and then, while maintaining contact between the test medium and the first section of the inner wall surface, applying various stresses to the tank as may be required by the test protocol. The sodium silicate solution of the test medium forms a protective film on the section of the inner wall surface in contact with the test medium that inhibits corrosion, so avoiding the severe damage to the walls and components within the tank that may otherwise occur on exposure to test medium containing source water. In one embodiment of the method of the present invention, the method includes forming the test medium by combining sodium silicate with deionized water. This step may include dissolving sodium silicate into the water. The step of forming the test medium may be performed outside of the internal containment are of the propellant tank to be tested. Alternatively, the step of forming the test medium may comprise the steps of introducing the water into the internal containment area of the tank and adding the silicate (e.g., by injection) to the internal containment area during the step of introducing the water. The method may further include the step of deionizing the water to be used in the test medium prior to combining with the silicate.

The present invention is adaptable to systems or structures in which an aqueous solution flows over, sprays, or immerses components, such as an inner wall of a tank or container, comprises metallic material, such as aluminum. It is adaptable for systems in which water or an aqueous solution, or a solid or semi-solid material containing water or stored in water, is contained or held within a container having walls comprising metallic materials such as aluminum, such as tanks, vats, bins, silos, pipes, vats, or sinks. It is also adaptable for systems in which a metal-containing surface is exposed to atmospheric conditions where the humidity level is not controlled.

BRIEF DESCRIPTION OF THE DRAWINGS

For a more complete understanding of the present invention, and the further advantages thereof, reference is now made to the following detailed description taken in conjunction with the drawings, in which.

DETAILED DESCRIPTION

In the following description, the invention is set forth primarily in the context of large space launch vehicle booster tanks, whose interior walls and components are fabricated primarily from aluminum alloys. The principles of the invention discussed with respect to space launch vehicle booster tanks, however, apply equally to application of the invention to other fluid containment vessels. By fluid containment vessel, it is meant that the structure at issue includes an interior volume designed to receive a fluid, such as for storage or for transmission of flow of the fluid. Examples of fluid containment vessels designed for transmission of flow of a fluid include pipes, conduits, valves, transducers, bellows, pumps and other flow fittings or propulsion components.

Furthermore, the following discussion focuses on application of the present invention is structural testing of large space launch vehicle booster tanks. The principles involving formation of corrosion-inhibiting silicate films and resulting vessels apply equally to other situations. The structural testing process is intended to evaluate the strength and integrity of the interior walls and components of the tanks. During this process, the tanks are substantially filled with a fluid medium, and the medium in then left in the tanks for an extended period of time. While filled with fluid medium, the tanks may be subjected to various forms of external and internal pressure. A preferred method of testing includes using source water as a fluid medium, primarily because it is inexpensive, easy to handle, and can be disposed without environmental concerns. A problem with using source water, however, is that when it comes into contact with certain metal surfaces, including those containing aluminum, the metal surface can become corroded.

The embodiment described herein is utilized with booster tanks of two varieties, the liquid oxygen (LOX) oxidizer booster tank, 13 feet in diameter and 58 feet in height, with a capacity of approximately 50,000 gallons, and the rocket propellant (RP) fuel booster tank, 13 feet in diameter and 32 feet in height, with a capacity of approximately 26,000 gallons. The inner wall surfaces of both types of tanks are comprised of aluminum alloy barrel panels fabricated in an isogrid pattern, such that the inner wall surfaces have a multiplicity of interconnecting ridges. The inner wall surfaces form an internal containment area, also interchangeably referred to herein as an internal fluid containment volume, which functions to hold the liquid oxygen or rocket propellant fuel material. Each tank has aft and forward domes, also fabricated of aluminum alloys. Because of the complexity of the inner wall surfaces of the tanks, it is not feasible to apply paint or other corrosion inhibiting material to such surfaces to protect the inner surfaces during structural testing. While the present embodiment is set forth in the context of launch vehicle booster tanks, the invention can be used with a wide variety of tanks, components, and other structures having metal-containing surfaces.

In the present embodiment, the inner wall surfaces of the booster tanks are fabricated from several aluminum alloys, such as 2014-T62 (forward and aft domes), 2014-T651 (barrel panels), 2219-T6 (outlet sump), and 7050-T7451 (manhole cover with stainless steel fasteners). The 2000 series aluminum alloys include copper as a major alloying element, and the 7000 series aluminum alloys include zinc as a major alloying element. The invention is not limited to these alloys, and it is contemplated that the invention may be applied to various metal compositions, with a greater or smaller or no aluminum content. In addition, while the embodiment of the invention described herein is primarily addressed to inhibiting corrosion of aluminum-containing metallic surfaces, the invention is applicable for use to protect other metal surfaces, including those comprised of stainless steel, alloy/carbon steel, and magnesium alloys, or a dissimilar metals assembly. It should be noted that the any non-metallic materials used in the present embodiment (structural testing) such as valves, pumps, etc., generally shall be free of plasticizers, particularly for a liquid oxygen system. Also, the method and system of the present invention may be applied to a smaller helium pressurization tank (with diameter of about three feet and length of about six feet), which is used to pressurize the rocket propellant and liquid oxygen to the rocket engine. This tank is fabricated of 6061-T6 aluminum alloy liner and carbon composite overwrap, and it is subject to hydrostatic pressure testing with an aqueous test medium. The 6000 series aluminum alloys include magnesium and silicon as major alloying elements.

Figure 1:
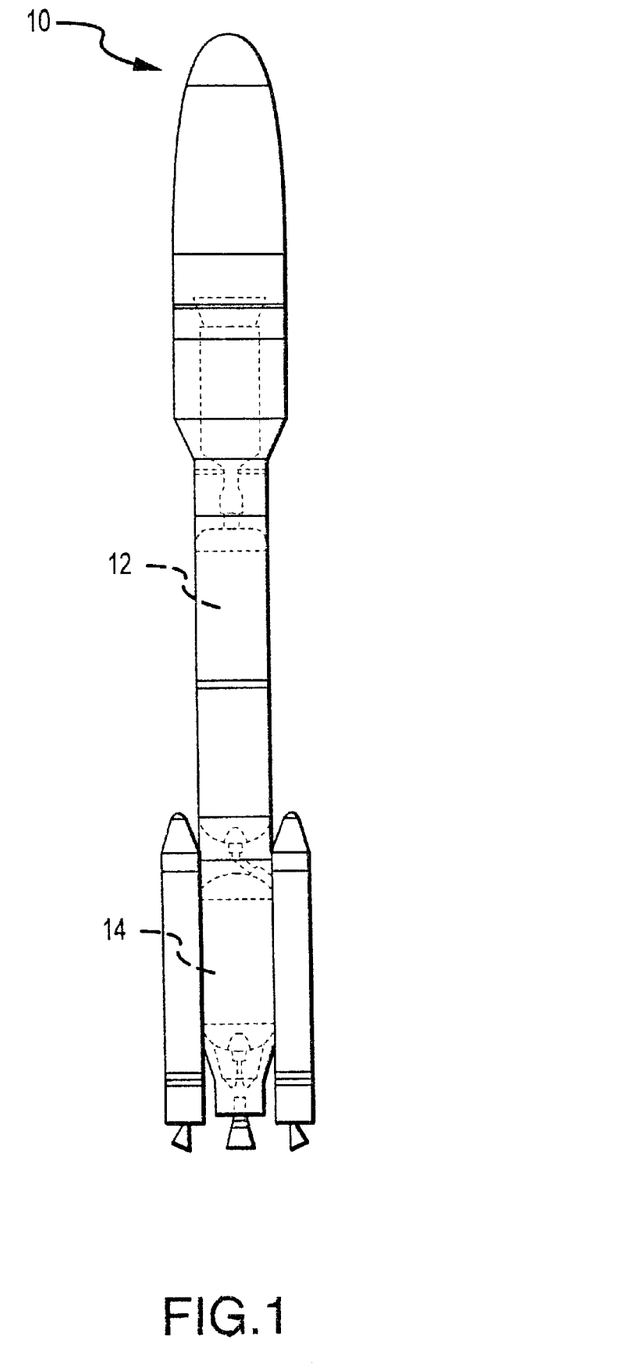
FIG. 1 is an external view of a launch vehicle.
Figure 2:
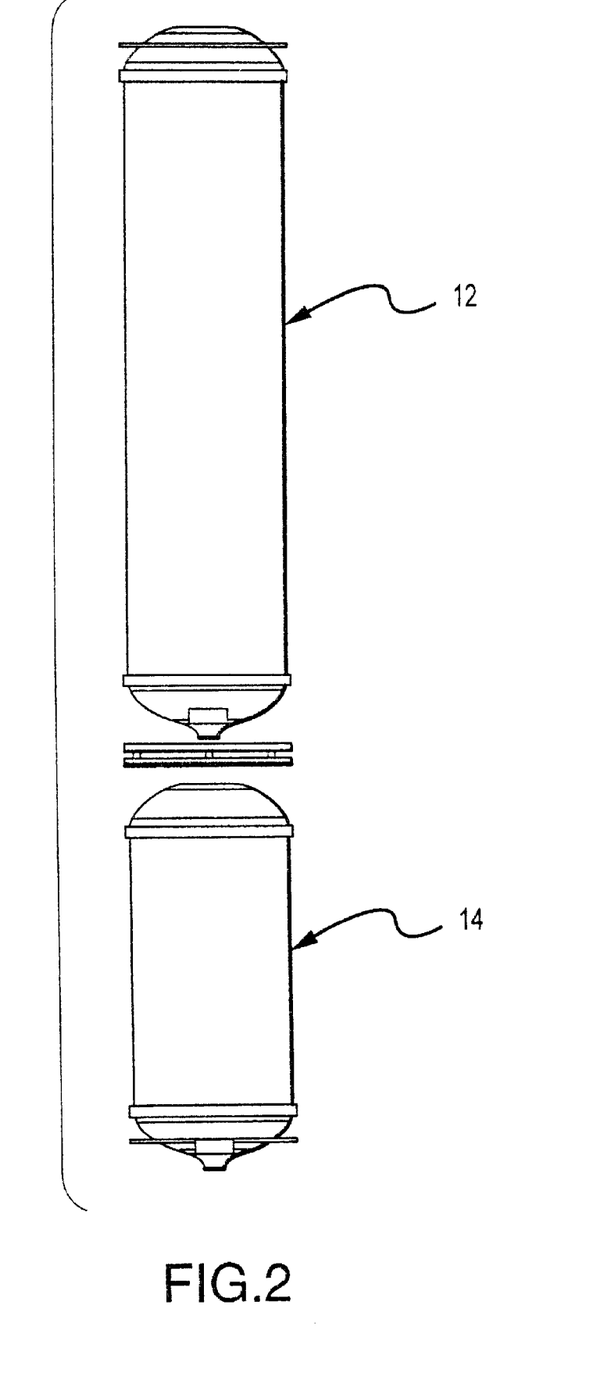
FIG. 2 is a perspective view of liquid oxygen and rocket propellant tanks, in which a structure test using a fluid medium might be performed.
Figure 3:
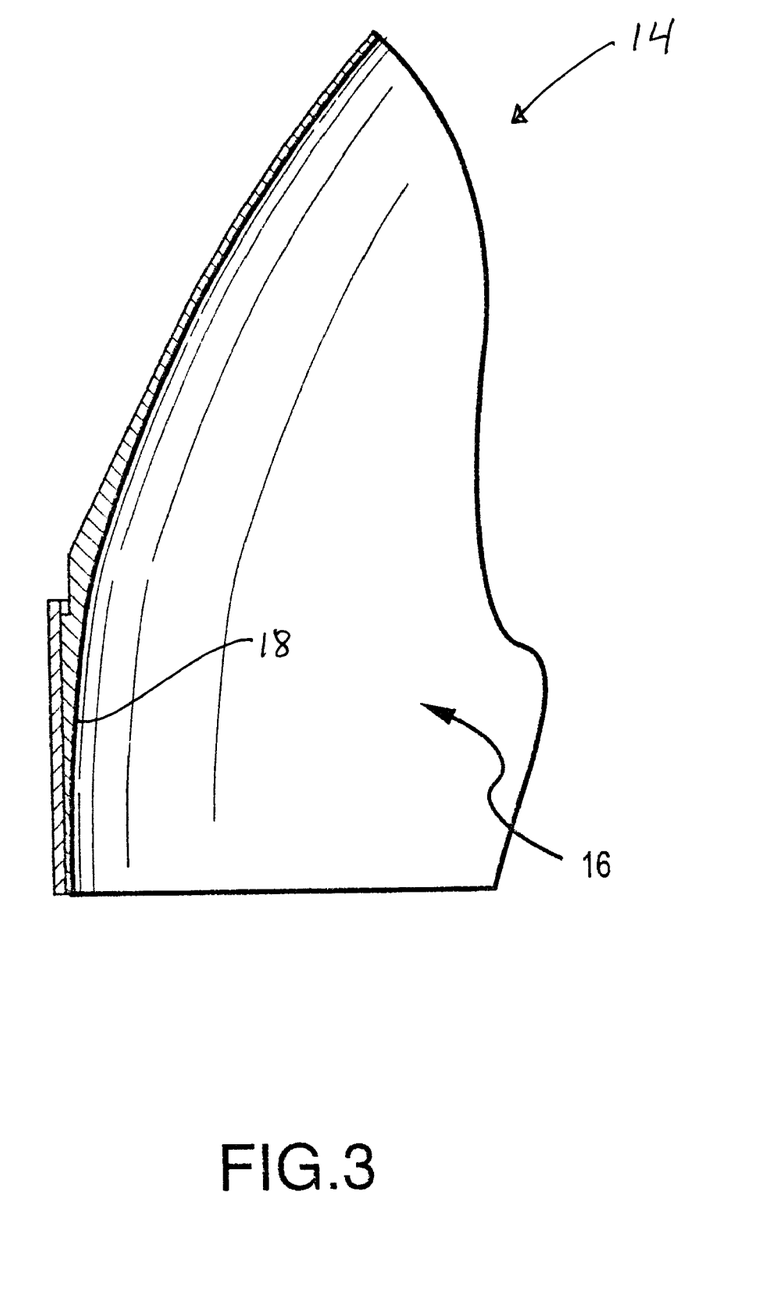
FIG. 3 is a perspective view of the inner wall surface of a propellant tank.
Figure 4:
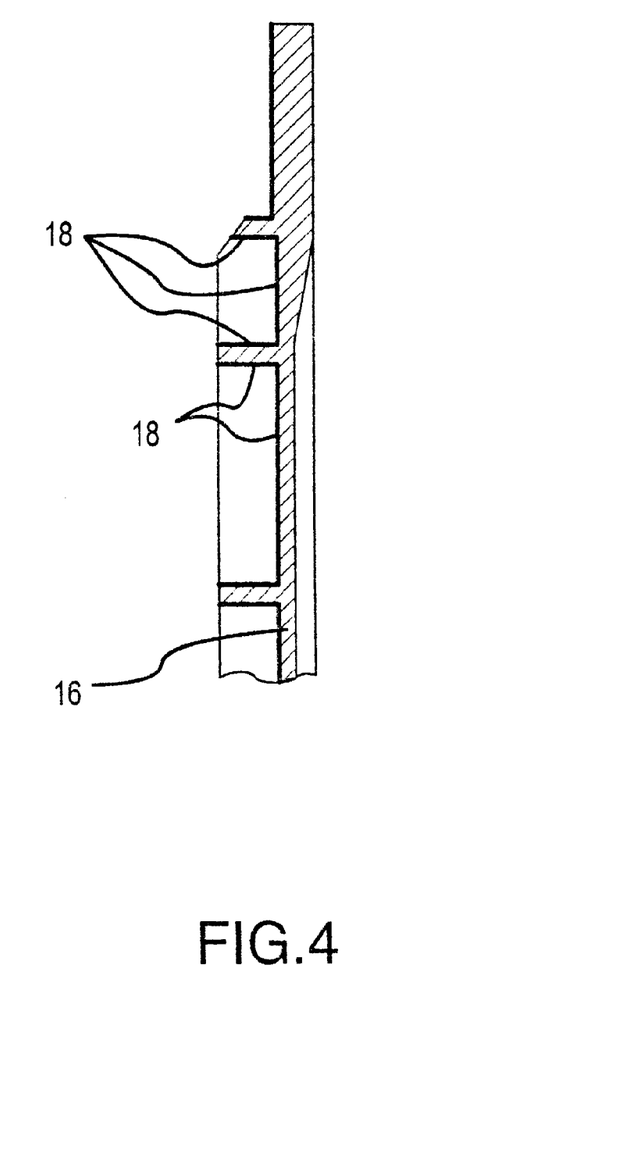
FIG. 4 is an enlarged partial cross-sectional view of the inner wall of a propellant tank, in which a thin silicate film has formed on the interior surface of such wall.

FIG. 1 is a view of a space launch vehicle 10 containing a liquid oxygen tank 12 and rocket propellant fuel tank 14. FIG. 2 depicts the liquid oxygen tank 12 and the rocket propellant tank 14. FIG. 3 is a perspective view of the inner wall of a barrel panel of the propellant fuel tank 14, having an inner wall surface 16. The liquid oxygen tank 12 (FIG. 1) is structurally similar to the propellant fuel tank 14 as shown in FIG. 2. In some instances, a propellant tank, such as the rocket propellant fuel tank 14 or the liquid oxygen tank 12 depicted in FIGS. 1 and 2, may be the subject to structural testing that includes contacting the inner wall surface 16 depicted in FIG. 3 with a fluid test medium comprising of water. The system and method of the present invention protects the inner wall surface 16 from corrosion that may occur during testing with an aqueous test medium by depositing a thin silicate film 18 on the inner wall surface 16. As used herein, a silicate film is any thin layer of material comprising oxygen, silicon and one or more metals. In the case of an aluminum-containing metallic surface, this silicate film comprises aluminum, oxygen and silicon. Compounds in the silicate film that include aluminum, oxygen and silicon are typically represented by the formula $Al_xO_ySi_z$, where x, y and z are independent of each other and represent the relative molar quantities of aluminum, oxygen and silicon in the silicate film. It should be appreciated, however, that the silicate film could include silicates of other metals in addition to aluminum, depending upon the composition of the metallic wall on with the silicate film is formed. FIG. 4 is an enlarged partial cross-sectional view of the inner wall surface 16 following contacting the surface with a fluid medium comprising sodium silicate, in which the protective silicate film 18 has formed on the inner wall surface 16.

In one aspect, the method of the present invention generally includes the step of contacting a test medium comprising water and an alkali metal silicate, typically dissolved in the water, with at least one aluminum alloy inner wall surface of a tank, the inner wall surface defining an internal containment area, to form a protective silicate film. While the test medium may comprise any of a variety of alkali metal silicates, a preferred source is sodium silicate. In one embodiment of the present invention, prior to the contacting step, the invention includes a step of removing gross contaminants (e.g., aluminum chips) from at least the inner wall surface, such as by rinsing the inner wall surface with water. Removal of gross contaminants is advantageous, because such contaminants may impair formation of the protective silicate film. In another embodiment of the present invention, the method includes, prior to the step of contacting the test medium, the step of forming the test medium by mixing an alkali metal silicate, such as sodium silicate, with water outside the tank. In another embodiment, the step of forming occurs prior to the step of contacting the test medium by injecting (such as by a pump) the alkali metal silicate into water as the water flows through a conduit connected to the internal containment area defined by the inner wall surface of the tank. As used herein, a silicate, or metal silicate, refers to any compound material including silicon, oxygen, and one or more metals. Sodium silicate, $xNa_2O \cdot ySiO_2$ may include varying x and y molal concentration, but the molar ratio of $SiO_2$ to $Na_2O$ varying from 0.2 to 3.75 is preferred, and with ratios in the upper portion of the range being more preferred for use with the present invention.

For purposes of further inhibiting corrosion, the test medium used for the step of contacting the medium comprises sodium silicate and deionized water. In this regard, the method may include, before the step of contacting the test medium with the inner wall surface, the step of deionizing source water to produce deionized water. The method may further include, before the step of contacting, the step of inspecting at least the inner wall surface for gross contaminants (e.g., aluminum chips), and/or removing gross contaminants by rinsing the inner wall surface with water. Conducting these inspecting and/or removing steps enhances formation of the protective film.

As applied to testing of tanks, the method of the present invention generally includes a further step of applying one or more structural or other stresses to at least one feature of the tank, such as would be done during static load testing, while at least one section of the inner wall surface of the tank is in fluid contact with the test medium. The method also includes the step of examining the tank for leakage from the tank and/or for other irregularities while the test medium is in fluid contact with at least one section of the inner wall surface. While the test process might occur over short periods of time, of a few minutes to a few hours, in one embodiment of the invention, the test occurs over a time of at least one week, often at least five weeks, and typically as long as about seven weeks, and the test medium remains in contact with the aluminum containing surface for that entire test period. It is anticipated that the test process could extend for periods in excess of seven weeks, with the test medium remaining in contact with the surface for these longer periods.

Tests of surfaces fabricated from the aluminum alloys typically used in launch vehicle booster tanks reveal that, if the test medium consists of source water only, substantial corrosion, including discoloration, pitting, and the formation of a white corrosive deposit on the surfaces and sediment in the test medium occurs. Corrosion tends to be severe when aluminum alloy surfaces are exposed to a test medium consisting of source water for extended periods. When deionized water is used as the test medium, the degree of corrosion is significantly lessened as opposed to that obtained with source water, although discoloration and formation of deposits and sediment may still occur. Accordingly, while the step of contacting the test medium with the inner wall surface of the tank could employ source water in the test medium, in a preferred embodiment, the test medium comprises deionized water. In the present embodiment, the preferred purity of deionized water is such that it meets the requirements of any Types I, II, III and IV described in the publication *Standard Specification for Reagent Water* (1997), also known as ASTM D1193, by the American Society for Testing and Materials or equivalent specification of deionized water. Other high purity sources of water could also be used, such as for example distilled water.

The concentration of the silicate dissolved in the aqueous liquid of the test medium may be different for different applications but will typically be very low. In the case of sodium silicate solutions, in most instances, the concentration of the dissolved sodium silicate will typically be smaller than about 5,000 parts per million (by weight) relative to the total weight of the test medium, preferably smaller than about 1,000 parts per million, more preferably smaller than about 500 parts per million, and most preferably smaller than about 250 parts per million. The concentration of the sodium silicate dissolved in the aqueous liquid of the test medium should, however, typically be large enough to provide a silicate film that substantially covers and protects the treated surface. The concentration of the dissolved silicate in the aqueous liquid of the test medium will typically be larger than about 1 part per million (by weight) relative to the total weight of the test medium, preferably larger than about 5 parts per million, and more preferably larger than about 10 parts per million. This discussion concerning sodium silicate concentrations in the test medium applies also to other metal silicates, such as other alkali metal silicates or alkaline earth silicates that may be used with the present invention instead of or in addition to sodium silicate.

In the present invention, the concentration of alkali metal silicate may be adjusted, depending upon the type of metal-containing surface, the degree of a corrosion resistance of the metallic surface used, the degree of purity of the water, and the length of time the test medium is expected to be in contact with metal-containing surface. In a preferred embodiment, which employs sodium silicate, the test medium is comprised of about 30 parts per million of a prime sodium silicate solution in deionized water by volume (of the purity described above), which results in aluminum alloy surfaces even after a period of time up to and including seven weeks, or more, substantially free of pitting corrosion, deposits and other severe corrosion. In one embodiment, the prime or first solution silicate solution comprises an aqueous sodium silicate solution, by weight: 20% to 40% sodium silicate, $Na_2O$ of 8.83% to 9.06%, $SiO_2$ of 29% to 29.4%, sulfates of less than 200 parts per million, chlorides at less than 350 parts per million, aluminum at less than 550 parts per million, iron at less than 80 parts per million, titanium at less than 100 parts per million, and other metallic constituents at less than 59 parts per million, and having a ratio of $SiO_2$ to $Na_2O$ of 3.23 to 3.29. Lower concentrations of this prime sodium silicate solution in deionized water by volume, in the range of between about 20 parts per million to about 30 parts per million, may be effective to substantially inhibit corrosion of surfaces containing certain metals that are more corrosion resistant (such as the 6000 series of aluminum alloys), and/or where shorter periods of exposure are contemplated. Concentrations of this prime sodium silicate solution in deionized water by volume, between about 30 parts per million and about 175 parts per million or more, produce strong corrosion-inhibiting effects in a range of aluminum alloys, including substantially no pitting corrosion, deposits or sedimentation, plus no discoloration at the end of a one-week and up to and including a seven-week test period, or more, under the conditions above described. While silicate in various forms may be used, a source of this prime sodium silicate solution suitable for use n the present invention is the commercially available Nalco 2513, a product of Nalco Chemical Company. It should be noted that, in the present invention, the method can be carried out at ambient temperatures, preferably in the temperature range of about 65 degrees Fahrenheit to 75 degrees Fahrenheit. In another embodiment, the test medium is a sodium silicate solution comprising sodium silicate in a concentration of between about 11 parts per million, by weight, and 117 parts per million, by weight, in deionized water, per Table 1 below.

TABLE 1

| Test medium parts per million by volume of first, or prime, sodium silicate solution | Test medium parts per million by weight of first, or prime, sodium silicate solution (approximate) | Test medium parts per million by weight of sodium silicate (based on 40% weight of sodium silicate in first, or prime, sodium silicate solution) |
|---|---|---|
| 20 | 28 | 11 |
| 30 | 42 | 17 |
| 175 | 244 | 97 |
| 210 | 292 | 117 |

An important factor of the present invention is that the silicate film is very thin, yet provides substantial protection against corrosion in mildly corrosive environments. This is particularly advantageous with aerospace applications, where weight minimization is particularly important. With the present invention, the silicate film has a thickness typically smaller than about 1000 angstroms, preferably smaller than about 500 angstroms, more preferably smaller than about 100 angstroms and most preferably smaller than about 50 angstroms. Typically however, the silicate film will have a thickness of at least about 10 angstroms. These thicknesses are as determined by any suitable technique, but preferably are as determined by x-ray photoelectron spectrographic analysis.

Analysis of surfaces fabricated from an aluminum alloy with copper alloying element after contact with a test medium solution of about 30 to 175 parts per million by volume of the prime sodium silicate solution in deionized water indicated that a thin protective film of AL—O—Si compound formed on such surfaces, having a thickness of about 25 angstroms when measured by X-ray photoelectron spectrographic analysis. It is believed that this film forms almost instantaneously after contacting the test medium with the surface, even at ambient temperature, such that a period of exposure of a few minutes would be adequate to form the protective film. Not to be bound by theory, it is believed that the silicate dissolved in the test medium quickly reacts with one or more metal of the metallic surface to form a silicate film. In the case of reaction between sodium silicate and aluminum, a film having a compound material generally of the formula $Al_xO_ySi_z$ is formed.

Figure 5:
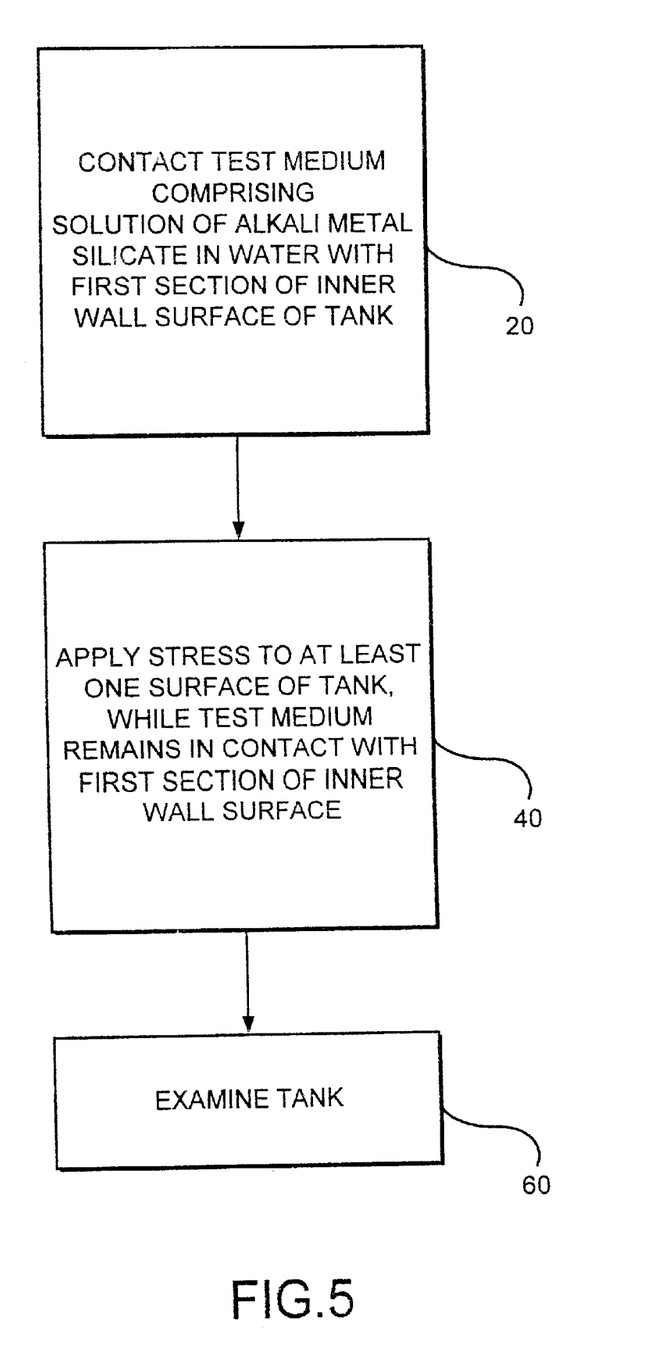
FIG. 5 is a flow chart of one embodiment of the method of the present invention.

FIG. 5 is a flow chart describing a generalized process for forming a protective silicate film comprised of AL—O—Si compound on the inner wall surface of a launch vehicle propellant tank to be subjected to structural testing, wherein the tank has an inner wall surface and an external wall surface. As noted in FIG. 5, the process includes the step 20 of contacting a test medium comprising a solution of alkali metal silicate in water with at least a first section of the inner wall surface of the tank to form a reaction product on the inner wall surface comprising at thin film of Al—O—Si compound. This film in turn inhibits corrosion to at least the first section of the inner wall surface caused by the ionic impurities in aerated water of the test medium. The step of contacting the test medium generally causes the water of the test medium to become aerated. The contacting typically involves filling a portion, and preferably substantially all, of the internal fluid containment volume with the test medium, so that at least a portion, and preferably substantially all of the metallic wall surface defining the fluid containment volume is treated. The process further includes the step 40 of applying stress to at least one of the inner wall surface (e.g., proximate the first section) and the external wall surface of the tank while the test medium remains in contact with at least the first section of the inner wall surface. The process further includes the step 60 of examining the tank (e.g., proximate the first section) for deformation, leakage and other irregularities.

Figure 6:
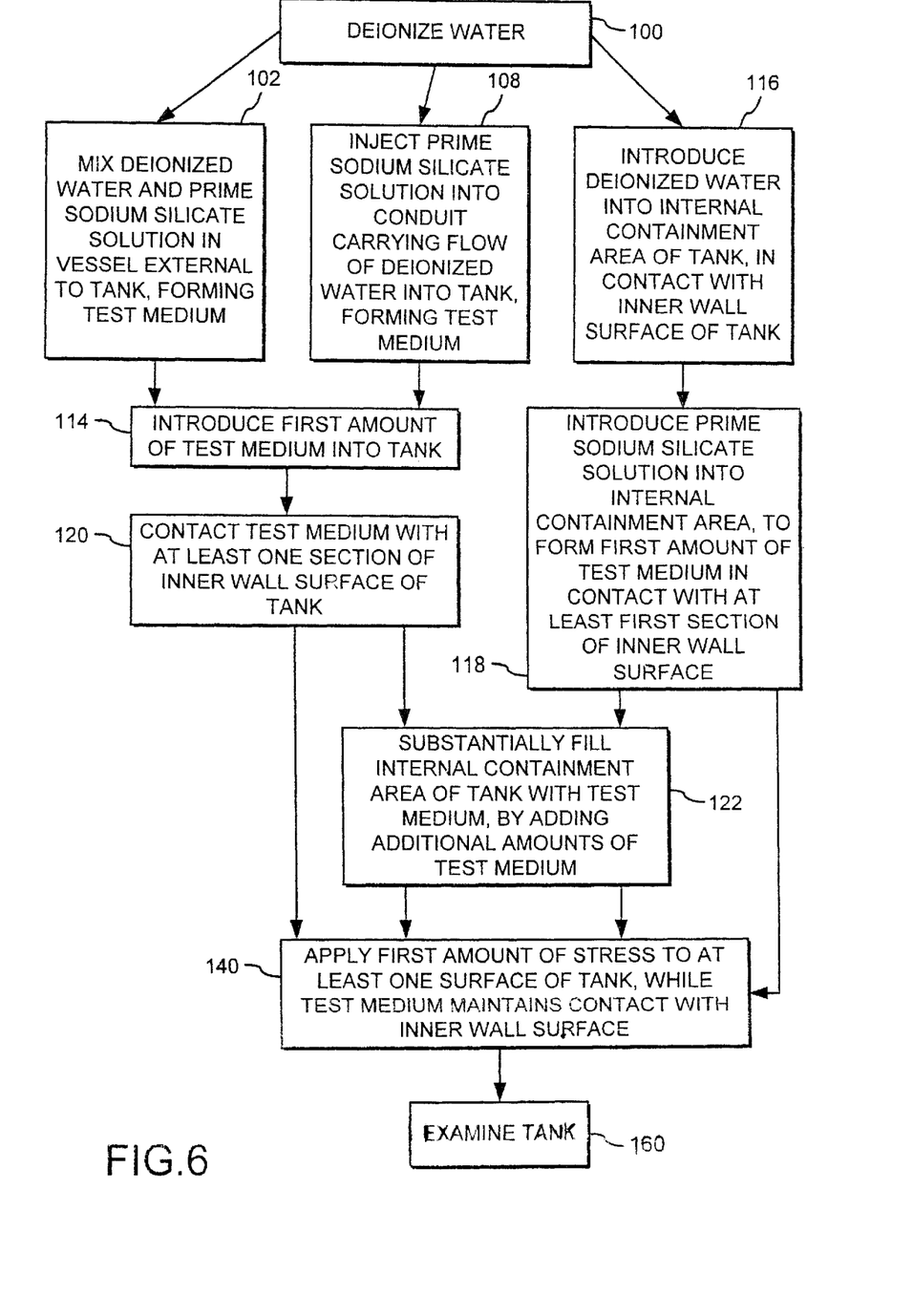
FIG. 6 is a flow chart of another embodiment of the method of the present invention.

FIG. 6 is a flow chart of another embodiment of the present method for testing a tank using an aqueous test medium, wherein a protective film formed by the test medium inhibits corrosion to the inner wall surface of the tank caused by the ionic impurities in aerated water in the test medium. The context for this flow chart is a launch vehicle propellant tank having an external wall surface and an inner wall surface, with the inner wall surface defining an internal containment area capable of holding the aqueous test medium. The method includes a step 100 of deionizing source water to form deionized water for use in forming the test medium. The method further includes a step 102 of mixing the prime sodium silicate solution and the deionized water in a vessel external to the tank to form a sodium silicate solution that will serve as the test medium, such that the desired concentration of the prime sodium silicate solution in deionized water is uniform across the test medium. Alternatively, the method may include a step 108 of injecting an amount of the prime sodium silicate solution into a conduit carrying deionized water into the tank, thereby forming the test medium in the conduit with a desired concentration of sodium silicate in the test medium. Following either of these steps, the method next includes a step 114 of introducing a first portion of test medium into the internal containment area of the tank to bring a first section of the inner wall surface of the tank in contact with the first portion of test medium, such fluid contact resulting in the formation of a silicate film comprised of Al—O—Si compound on the first section of the inner wall surface. A further alternative, shown on FIG. 6, includes the step 116 of introducing deionized water into the internal containment area of the tank, so that it contacts as least one section of the inner wall surface of the tank, and then the step 118 of introducing an amount of the prime sodium silicate solution into the internal containment area to form a sodium silicate solution with the deionized water that serves as the test medium, having a desired silicate concentration uniform across the solution in contact with the inner wall surface of the tank. The method includes a step 140 of applying a first amount of stress to a least one surface of the tank, while the test medium remains in contact with the inner wall surface. Alternatively, the method includes the step of substantially filling the internal containment area of the tank, so that the test medium contacts substantially all sections of the inner wall surface of the tank, prior to the step 140 of applying stress. While there are various ways of applying stress to one or more surfaces of the tank, depending on the test process used, in the present embodiment, these may include applying a static load to the external wall surface or applying acoustic waves to the tank or applying sinusoidal forces to the test medium for a slosh damping test, or applying internal pressure to the inner wall surface by injecting an inert gas, nitrogen gas or dry air to raise the internal pressure bearing on the inner wall surface above the ambient pressure of the area surrounding the tank. The internal pressure may be raised by a pressurization pump. Finally, the method includes a step 160 of examining the tank (e.g., the external wall surface) for deformation, leakage or other irregularities.

Figure 7:
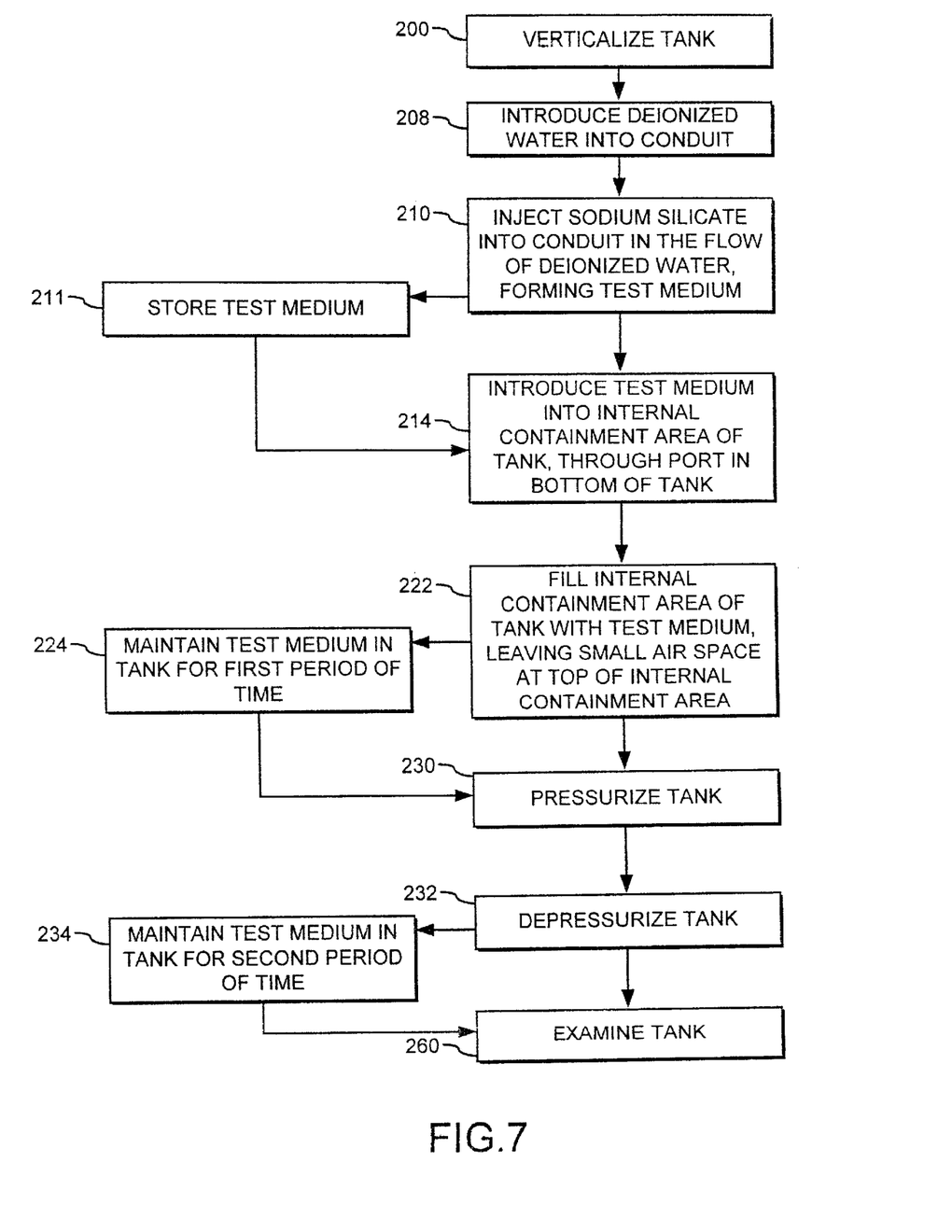
FIG. 7 is a flow chart of a further embodiment of the present invention, as applied to proof pressure hydrostatic testing of a launch vehicle propellant tank.

FIG. 7 describes another embodiment of the method of the present invention, which includes use of an aqueous test medium in proof pressure hydrostatic testing of a launch vehicle propellant tank. The booster tank has top and bottom ends, and has an external wall surface and an inner wall surface. The inner wall surface is comprised of aluminum alloy, and defines an internal fluid containment area capable of holding an aqueous test medium. The bottom end of the tank has a port through which test medium can enter and be drained from the internal containment area of the tank. This embodiment contemplates that the test medium is formed in a conduit attached to the port and then is transported through the conduit into the port and from there into the internal containment area. As noted in FIG. 6, the method involves the step 200 of first verticalizing the tank. The method then includes the steps of 208 introducing deionized water (formed, for example, by deionization of source water) into the conduit and 210 injecting prime sodium silicate solution. The turbulence of the test medium in the tank due to flow pressure further homogenizes the test medium. The next step 214 includes contacting the test medium with the inner wall surface by introducing the test medium into the internal containment are of the tank, from the conduit and through the port located in the bottom end of the tank. In a preferred embodiment, the test medium is introduced at the bottom end of the tank to reduce the likelihood that air pockets will form on the inner wall surface. Such air pockets may adversely affect the testing process and formation of the protective silicate film. Note that a vent hole in the manhole cover helps to vent air while tank is being filled with medium. In another preferred embodiment, the test medium is introduced at a high pressure by a pressure pump to facilitate filling of the tank with test medium in an expedited manner (e.g., when introduced from a storage vessel as described below.) The method then includes the step 222 of substantially filling the internal fluid containment area of the tank, bringing the test medium in contact with virtually all sections of the aluminum alloy inner wall surface of the tank, and leaving a small air space at the top of the internal containment area. The method includes the alternative step 224 of maintaining the test medium in the tank for a first period of time, preferably of about three days or less. While the tank is still filled with test medium, the method includes the step 230 of pressurizing the tank, to increase the internal pressure bearing on the inner wall surface. This is preferably done by injecting nitrogen gas or dry air, to raise the internal pressure (for the specific launch vehicle tanks discussed herein in the range of about 80 pounds per square inch for about five minutes). Other methods of pressurization using other gases may be utilized. After the step 230 of pressurizing the tank, the method next includes the step 232 of depressurizing the tank, to return the internal pressure to atmospheric pressure. The method includes an alternative step 234, following said depressurizing step 232, of maintaining the test medium in the tank for a second period of time, preferably of about three days or less. In another embodiment of the invention, the internal containment area of the tank may be completely (100%) filled with test medium, up to the manhole cover opening (without any air gap) and then the tank can be pressurized with a pressure pump. In the present embodiment, the next step includes a step 260 of examining the tank for deformation, leakage and other irregularities. The description above, concerning composition of the test medium, forming the test medium, and additional uses and applications are all also applicable to static load testing of launch vehicle propellant tanks.

An advantage of the present invention in the field of space launch vehicles is that the silicate used is not felt to product a fire hazard and is consistent with applicable government requirements for liquid oxygen and other systems. A further advantage of the invention is that, following testing and removal of the test medium, the protective Al—O—Si film remains on the aluminum alloy inner wall surfaces of the propellant tanks, providing further protection from atmospheric moisture during storage and transportation prior to use on the launch pad. In addition, after use, the test medium containing silicate may be disposed as waste water, at silicate concentrations of 210 parts per million or less of prime sodium silicate solution, and after bring the pH to a range of about pH 6.5 to pH 8.0 without environmental concerns (this requirement may vary from jurisdiction to jurisdiction).

In another aspect of the invention the sodium silicate test medium may be recycled after initial use. The solution may be prepared and stored for use later, as for example, to meet production requirements. More specifically, in instances where a number of tanks will be processed, the step of injecting 210 may be followed by the step 211 of storing the test medium in a storage vessel as illustrated in FIG. 7. Storage of more than six weeks or recycling after an extended period of use in testing may require a further step of adding an anti-bacterial treatment to the solution.

A silicate solution with a concentration of silicate in deionized water in the range described above may be used to form a protective film on components with aluminum-containing, stainless steel, carbon/alloy steel, or other metallic surfaces. The solution also may be used to protect the interior walls of other fluid containment vessels such as pipelines, tubes, fitting, valves, pumps, and other equipment during testing or other processes where an aqueous medium is employed. The invention is adaptable for systems or structures in which an aqueous solution flows over, sprays, or immerses components whose outer walls consist of aluminum-containing or other metallic surfaces. The Al—O—Si film protects the metal surface underlying the film against normal atmospheric conditions (such as humidity). It is also adaptable for storage systems in which water or a mild aqueous solution, or a solid or semi-sold material containing water or stored in water, is held in a container having walls comprised of aluminum or other metallic materials, such as tanks, vats, bins, silos, pipes, vats or sinks.

Although the invention has been described primarily with reference to structural testing of a fluid containment vessel, it should be recognized that the invention is not so limited. For example, the silicate film need not be formed on the inner wall surface as part of structural testing. In one aspect the present invention provides a method for inhibiting corrosion involving contacting the surface to be protected with a treating fluid, which includes a silicate dissolved in an aqueous liquid, consistent with the previous discussion concerning the test medium used for structural testing. In another aspect, the invention provides a fluid containment vessel having an internal metallic wall surface covered at least in part by a silicate film according to the method of the invention, as previously discussed with respect to structural testing. In yet a further aspect, the invention provides a space launch vehicle having storage tanks for propellant oxidizer and propellant fuel, with at least one and preferably both of the tanks including the silicate film to provide internal corrosion-inhibiting protection. The oxidizer and the fuel are capable of being reacted in the space launch vehicle to propel the vehicle. Any suitable oxidizer/fuel combination may be used. One preferred oxidizer is liquid oxygen and one preferred fuel is a petroleum distillate, such as kerosene. Furthermore, the oxidizer tank and the fuel tank in the space launch vehicle are typically very large, such as larger than about 10,000 gallons each. These large tanks, and especially those without a smooth surface, such as is the case with an isogrid pattern, are particularly well suited for use with the present invention.

While various embodiments of the present invention have been described in detail, it is apparent that further modifications and adaptations of the invention will occur to those skilled in the art. However, it is to be expressly understood that such modifications and adaptations are within the spirit and scope of the present invention. Furthermore, any feature of any embodiment of the present invention described herein may be combined in any compatible way with any other feature of any other embodiment.

What is claimed is:

1. A booster tank for a space launch vehicle, the booster tank comprising:
   a metal wall with an inner wall surface forming an internal containment area within the booster tank;
   a silicate film on the inner wall surface, the silicate film inhibiting corrosion of the inner wall surface.

2. The booster tank of claim 1, wherein the metal wall is made of an aluminum-containing metallic material.

3. The booster tank of claim 2, wherein the aluminum-containing metallic material is an aluminum alloy.

4. The booster tank of claim 3, wherein the metal wall is comprised of a plurality of aluminum-alloy barrel panels.

5. The booster tank of claim 1, wherein the inner wall surface comprises an isogrid pattern having a multiplicity of interconnecting ridges.

6. The booster tank of claim 1, wherein the silicate film comprises an Al—O—Si compound.

7. The booster tank of claim 1, wherein the tank has a capacity of at least 26,000 gallons.

8. The booster tank of claim 1, wherein the silicate film has a thickness of about 25 angstroms as measured by X-ray photoelectron spectrographic analysis.

9. A space launch vehicle comprising the booster tank of claim 1.

10. The space launch vehicle of claim 9, wherein the booster tank is filled with a fluid selected from the group consisting of a rocket propellant fuel and liquid oxygen, the fluid being in contact with the silicate film.

11. A space launch vehicle comprising a plurality of the booster tank of claim 1, wherein:
    a first said booster tank contains a rocket propellant fuel in contact with the silicate film of the first said booster tank;
    a second said booster tank containing liquid oxygen in contact with the silicate film of the second said booster tank.

* * * * *